US008157772B2

(12) United States Patent  
Lewis

(10) Patent No.: US 8,157,772 B2  
(45) Date of Patent: Apr. 17, 2012

(54) MEDICAMENT DISPENSING DEVICES AND METHODS

(75) Inventor: Michael I. Lewis, Bryn Mawr, PA (US)

(73) Assignee: Cyto-Biotics, LLC, Bryn Mawr, PA (US)

( * ) Notice: Subject to any disclaimer, the term of this patent is extended or adjusted under 35 U.S.C. 154(b) by 0 days.

(21) Appl. No.: 12/377,899

(22) PCT Filed: May 8, 2008

(86) PCT No.: PCT/US2008/063112

§ 371 (c)(1),
(2), (4) Date: Feb. 18, 2009

(87) PCT Pub. No.: WO2008/138007

PCT Pub. Date: Nov. 13, 2008

(65) Prior Publication Data

US 2010/0234826 A1    Sep. 16, 2010

Related U.S. Application Data

(63) Continuation-in-part of application No. 11/800,812, filed on May 8, 2007, now abandoned.

(51) Int. Cl.
*A61M 5/315* (2006.01)

(52) U.S. Cl. .......................................... 604/218; 433/90

(58) Field of Classification Search .......... 604/218–231, 604/72; 433/90
See application file for complete search history.

(56) References Cited

U.S. PATENT DOCUMENTS

| | | |
|---|---|---|
| 37,486 A | 1/1863 | Benson |
| 695,356 A | 3/1902 | Washburn |
| 935,415 A | 9/1909 | Sands |
| 948,057 A | 2/1910 | Kline et al. |
| 1,642,950 A | 9/1927 | Haas |
| 1,878,513 A | 9/1932 | Haas |

(Continued)

FOREIGN PATENT DOCUMENTS

WO    WO 03/082139    10/2003

(Continued)

OTHER PUBLICATIONS

International Search Report and Written Opinion, prepared by the Korean Intellectual Property Office as International Searching Authority for PCT Application No. PCT/US2008/063112, mailed Oct. 13, 2008.

(Continued)

*Primary Examiner* — (Jackie) Tan-Uyen T. Ho
*Assistant Examiner* — Imani Hayman
(74) *Attorney, Agent, or Firm* — Swanson & Bratschun, L.L.C.

(57)    ABSTRACT

A medicament dispensing device including a substantially rigid carpule body which has a dispensing end and an actuation end opposite the dispensing end. The carpule body is substantially tubular and thus defines a carpule bore. The device further includes a plunger operatively disposed within the carpule bore having a plunger actuator near the actuation end of the carpule body and a plunger tip opposite the plunger actuator. The plunger tip and an orifice at the dispensing end of the carpule bore define a medicament volume which may be loaded with a medicament selected to achieve specific therapeutic goals. The carpule body may also include a wound depth scale. The depth scale is typically associated with the dispensing end of the carpule body. Similarly, the medicament dispensing device may include a dosage scale. Also disclosed are methods of dispensing medicaments.

30 Claims, 6 Drawing Sheets

U.S. PATENT DOCUMENTS

| | | |
|---|---|---|
| 1,905,752 A | 4/1933 | Rees |
| 2,151,418 A | 3/1939 | Bolte |
| 2,223,611 A | 12/1940 | Gross |
| 2,575,425 A | 10/1948 | Nelson |
| 2,537,550 A | 1/1951 | Roos |
| 2,672,144 A | 3/1954 | Cohen |
| 2,923,442 A | 2/1960 | Maras |
| 3,045,679 A | 7/1962 | Goldberg |
| 3,831,603 A | 8/1974 | Armenti |
| 3,831,605 A | 8/1974 | Fournier |
| 3,837,284 A | 9/1974 | Waldeisen |
| 4,472,141 A * | 9/1984 | Dragan ................... 433/90 |
| 4,585,439 A | 4/1986 | Michel |
| 4,645,487 A | 2/1987 | Shishov et al. |
| 4,664,655 A | 5/1987 | Orentreich et al. |
| 4,678,107 A | 7/1987 | Ennis, III |
| 4,808,166 A | 2/1989 | Davidov |
| 5,129,824 A | 7/1992 | Keller |
| 5,165,890 A * | 11/1992 | Discko, Jr. .................. 433/90 |
| 5,292,307 A | 3/1994 | Dolzine et al. |
| 5,445,523 A | 8/1995 | Fischer |
| 6,656,164 B1 | 12/2003 | Smith |
| 6,682,348 B2 | 1/2004 | Lawter et al. |
| 6,976,842 B1 | 12/2005 | Miggantz |
| 7,060,048 B1 | 6/2006 | Nat et al. |
| 7,086,861 B2 | 8/2006 | Pitz et al. |
| 7,699,609 B2 | 4/2010 | Lawter et al. |
| 2003/0186191 A1 | 10/2003 | Lawter et al. |
| 2010/0057005 A1* | 3/2010 | Aravena et al. ............ 604/135 |

FOREIGN PATENT DOCUMENTS

WO   WO 2004/006798   1/2004

OTHER PUBLICATIONS

European Search Report and Search Opinion for EP Application No. 08780607.1, mailed Jul. 2, 2010.

* cited by examiner

MEDICAMENT DISPENSING DEVICES AND METHODS

CROSS-REFERENCE TO RELATED APPLICATIONS

This application is a submission under 35 U.S.C. §371 of PCT Application Serial No. PCT/US2008/063112, filed May 8, 2008, currently pending, entitled "Medicament Dispensing Devices and Methods," which claims priority to and is a continuation-in-part of U.S. application Ser. No. 11/800,812, filed May 8, 2007, entitled "Unit Dose Dry Powder Ejection Carpule," which are each incorporated herein in their entirety by reference.

TECHNICAL FIELD

A medicament dispensing device and method, in particular, a medicament dispensing device suitable for manual use or for use with a medicament dispensing gun.

BACKGROUND

Unit dose medical and dental medicament delivery systems have been used for many years. In particular, unit dose delivery systems have been used in dentistry to dispense topical and subdermal antibiotic medicaments for the treatment of dental wounds. Known devices typically must be used with a medicament dispensing gun. In addition, typical prior art devices provide no functionality for the dispensing of a partial dose of the selected medicament.

The treatment of certain types of wounds or conditions requires the insertion of a medicament delivery device to a specific subdermal depth to achieve best results. Prior art dispensing devices in many cases provide little or no control over the depth of medicament insertion. The present invention is directed toward overcoming one or more of the problems discussed above.

SUMMARY OF THE EMBODIMENTS

One embodiment disclosed herein is a medicament dispensing device including a substantially rigid carpule body which has a dispensing end and an actuation end opposite the dispensing end. The carpule body is substantially tubular and thus defines a carpule bore. The device further includes a plunger operatively disposed within the carpule bore having a plunger actuator near the actuation end of the carpule body and a plunger tip opposite the plunger actuator. The plunger tip and an orifice at the dispensing end of the carpule bore define a medicament volume which may be loaded with a medicament selected to achieve specific therapeutic goals.

The actuation end of the medicament dispensing device may include an enlarged head adapted to be received in a medicament dispensing gun. Alternatively, the actuation end may include or be associated with a plunger extension which provides for or facilitates the manual actuation of the plunger actuator. The plunger actuator may be recessed or otherwise configured to avoid accidental actuation. Thus, the medicament dispensing device embodiments as described herein are well-suited for the emergency treatment of wounds and other traumatic injuries with manually actuated embodiments and the treatment of non-emergency conditions with dispensing gun actuated embodiments.

In an embodiment which features a plunger extension, the medicament dispensing device may further include an attachment ring or other structure connecting the plunger extension in sliding engagement with the carpule body. The carpule body may also include a wound depth scale. The depth scale is typically associated with the dispensing end of the carpule body.

Similarly, the medicament dispensing device may include a dosage scale. The dosage scale may be associated with the actuation end of the carpule body. Other locations for the dosage scale are within the scope of the present disclosure. In one representative but non-limiting embodiment the dosage scale will include indicia associated with a notch at or near the actuation end of the carpule body. The notch may further be operatively associated with the plunger actuator. The indicia facilitate the selective delivery of a partial dosage of the medicament. In this representative embodiment, the bottom of the notch may define a stop which limits the travel of the plunger actuator and thus limits the quantity of medicament which may properly be delivered at full dosage.

The medicament dispensing device may include a plunger tip which has substantially the same diameter as the orifice. In addition, the plunger tip may define a concave or concave-shovel surface facing the orifice. This configuration is particularly well-suited for the dispensing of powdered medicaments, such as powdered topical antibiotics. The carpule body near the dispensing end may be tapered, rounded, or otherwise shaped to facilitate insertion of the medicament dispensing device into a wound, or other treatment site. The dispensing end may be rigid and non-deformable.

It may be desirable for specific embodiments or to achieve specific treatment goals that the carpule body be angled along its length. An angle along the length of the carpule body such that the central axis of the actuation and dispensing ends of the carpule body define an angle of between 100 and 120 degrees may be advantageous. An angle of 115 degrees may be particularly advantageous.

The medicament dispensing device may include a protective cover. The protective cover may cover the entire carpule body, plunger extension, or any other apparatus associated with the dispensing device. Alternatively, the protective cover may cover and protect only a portion of the medicament dispensing device, for example the dispensing end, and any medicament contained therein. The protective cover may further include apparatus which facilitates the removal of same, for example a tab and scored seam.

Another embodiment disclosed herein is a method of dispensing medicament. The method includes providing a device as described above to a user. The user may then insert the medicament dispensing device into a site to a selected depth of insertion. The depth of insertion may be verified with a depth scale associated with the medicament dispensing device as described above. The method may then include depressing the plunger to dispense pre-loaded medicament into the site.

As used herein, a site may be a wound or other trauma site where it is desired to dispense topical antibiotic or other emergency care type medicaments. Alternatively, a site may be any place on a human or animal body where it is desired to dispense a specific quantity of medicament. For example, a site may be a periodontal pocket.

The plunger may be depressed to dispense medicament by the actuation of a medicament dispensing gun. Alternatively, the plunger may be depressed by manual actuation, for example, with a plunger extension or similar apparatus. The manual actuation of a plunger extension may be facilitated by attaching the plunger extension to the medicament dispensing device with a sliding engagement.

The method may further include dispensing a partial dose of the medicament. Verification of the dispensing of a partial dosage may be made with a dosage scale associated with the medicament dispensing device. Alternatively, full dosage of the medicament may be administered by depressing the plunger into engagement with a plunger stop. The method may further include removing a protective cover from the device prior to use.

DETAILED DESCRIPTION

Figure 1:
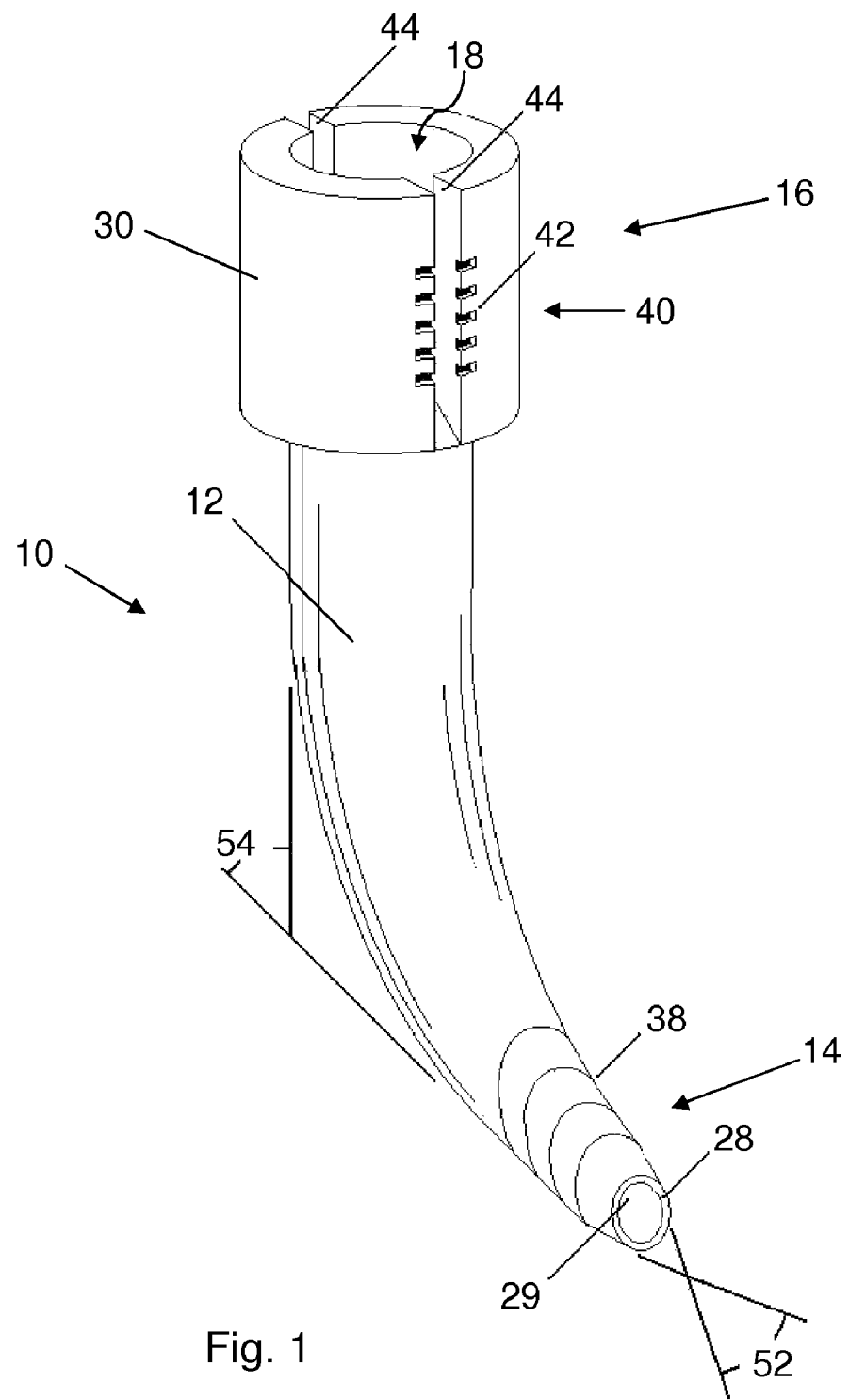
FIG. 1 is a perspective view of a medicament dispensing device.

One embodiment disclosed herein is a medicament dispensing device 10 having a substantially rigid carpule body 12. As shown in FIG. 1, the carpule body 12 includes a dispensing end 14 and an actuation end 16. The carpule body 12 is substantially tubular, accordingly the carpule body 12 defines a carpule bore 18.

Figure 2:
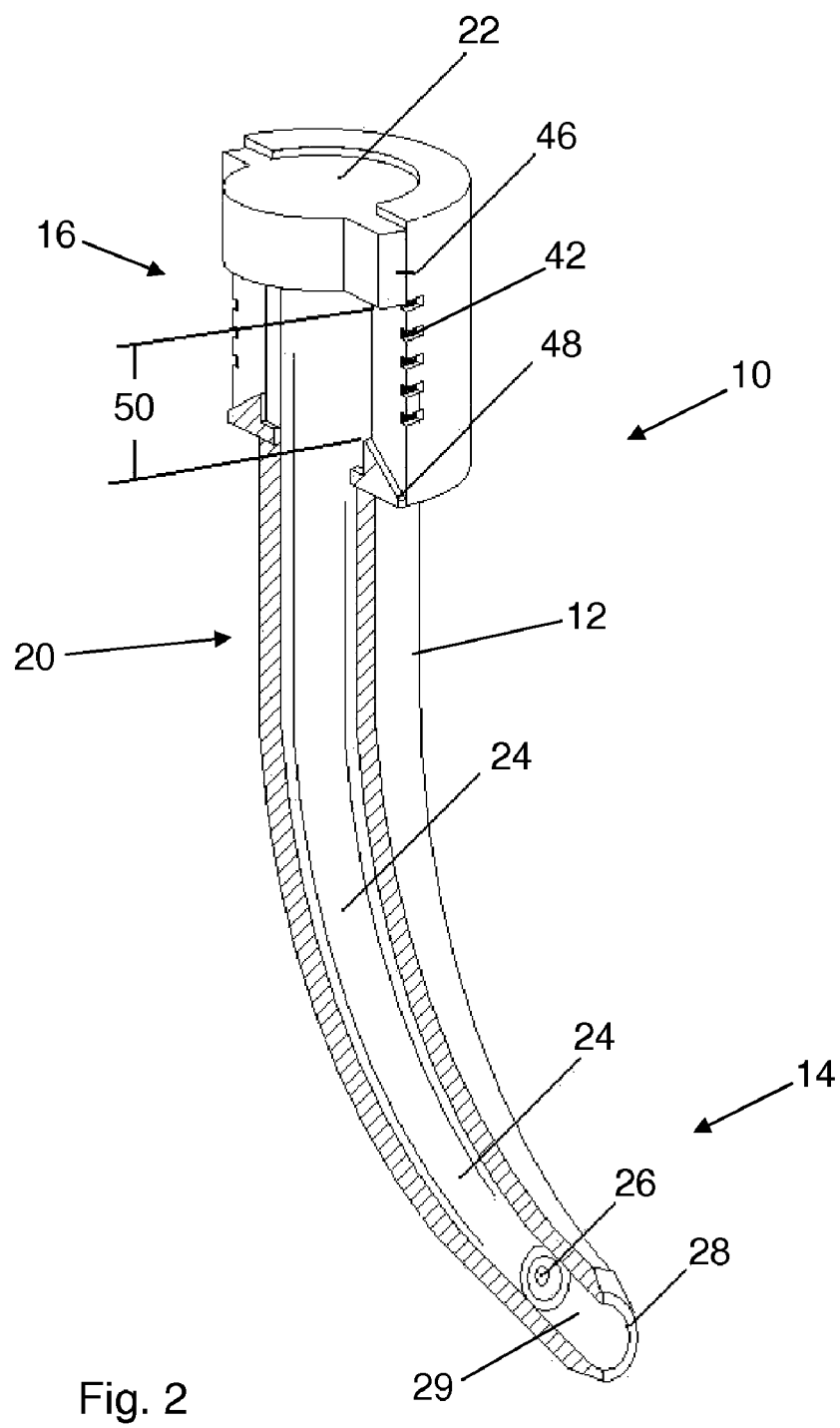
FIG. 2 is a longitudinal section view of the medicament dispensing device of FIG. 1 along the axis of the carpule bore.

The medicament dispensing device 10 also includes a plunger 20 operatively positioned within the carpule bore 18. As shown in FIG. 2, the plunger 20 includes a plunger actuator 22 which is operatively positioned near the actuation end 16 of the carpule body 12. The plunger also includes a flexible plunger shaft 24 extending from the plunger actuator 22 to a plunger tip 26 at the opposite end of the plunger from the plunger actuator 22. The plunger actuator 22 may be recessed or otherwise configured to prevent accidental actuation.

As is described in further detail herein the plunger is positioned in sliding engagement with the carpule bore 18. Typically, the plunger 20 will be positioned toward the actuation end of the carpule body prior to use of the medicament dispensing device 10 for the dispensing of a selected medicament. In use the plunger 20 will be moved lengthwise through the carpule bore 18 toward the dispensing end 14 of the carpule body 12. Accordingly, when the medicament dispensing device 10 is configured to dispense a medicament, the plunger tip 26 and a portion of the carpule bore 18 at the dispensing end 14 will define a medicament volume 27 into which selected medicaments may be placed and stored. An orifice 28 is defined by the carpule body at the dispensing end for the dispensing of a selected medicament.

As is described in detail herein, the medicament dispensing device 10 may be configured for use with a conventional medicament dispensing gun. Alternatively, the medicament dispensing device 10 may be configured for the manual dispensing of a medicament without the assistance of an external apparatus such as a dispensing gun. Referring to FIG. 1, the actuation end 16 of the carpule body 12 may include an enlarged head 30 configured and shaped to be received in an appropriate socket associated with a medicament dispensing gun (not shown on FIG. 1). In this embodiment, the carpule bore 18 will typically extend through the enlarged head 30 allowing the appropriate plunger or other apparatus associated with the medicament dispensing gun ready access to the plunger actuator 22.

Figure 3:
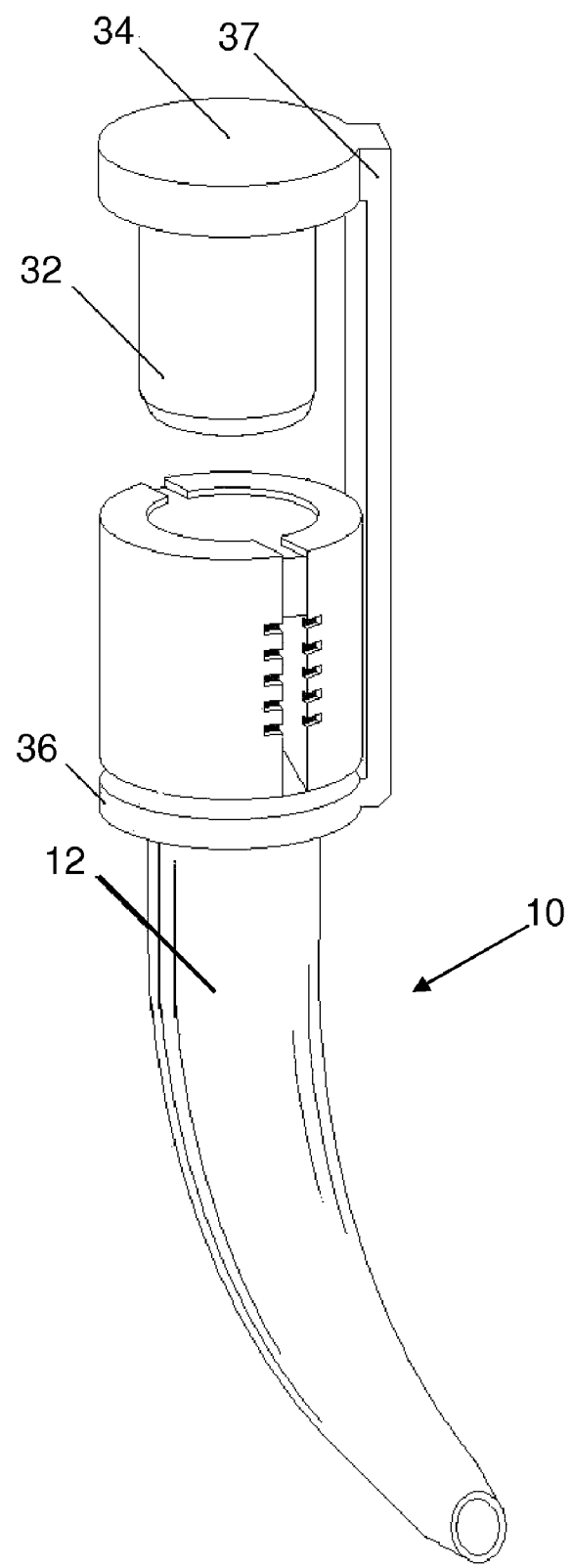
FIG. 3 is a perspective view of a medicament dispensing device suitable for self-actuation and the treatment of wounds.
Figure 4:
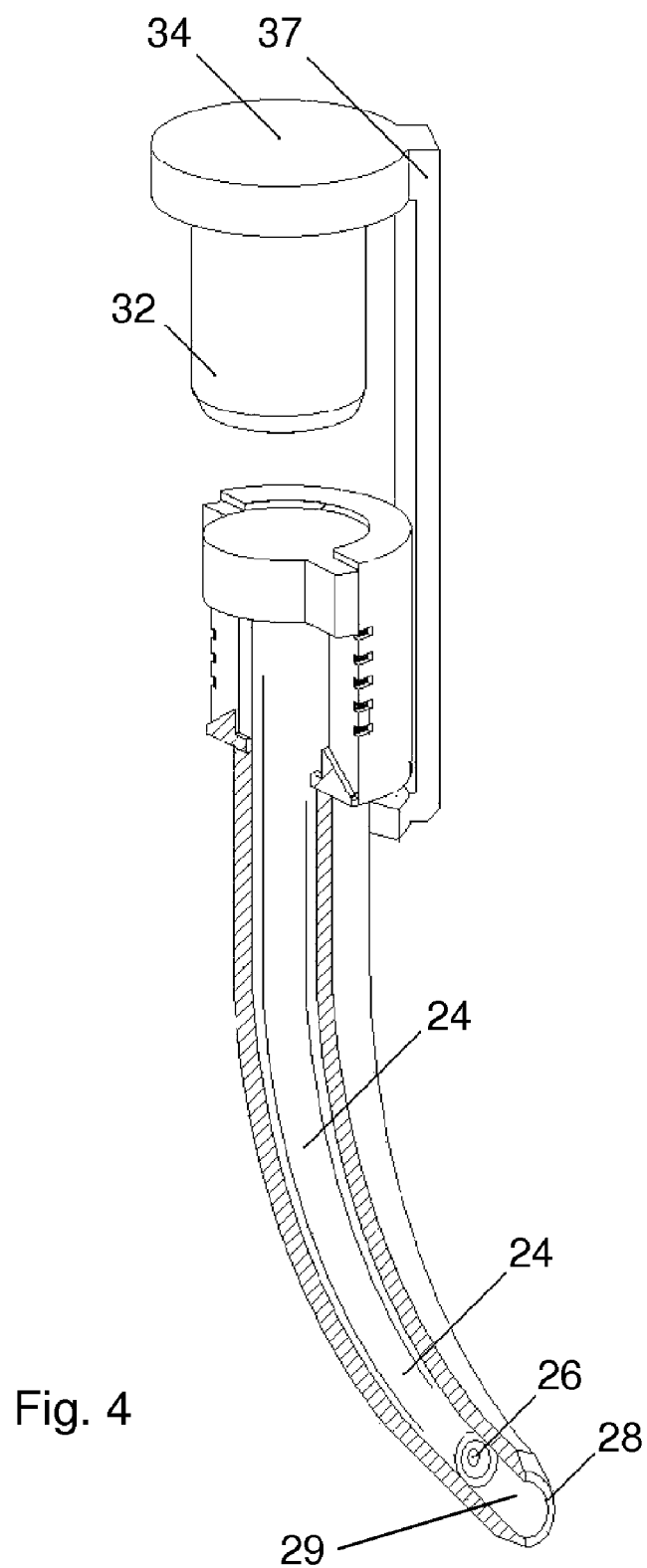
FIG. 4 is a longitudinal section view of the medicament dispensing device of FIG. 3 along the axis of the carpule bore.

Alternatively, as is best shown on FIGS. 3 and 4, the medicament dispensing device 10 may be configured for manual actuation. Manual actuation is particularly advantageous in an embodiment of the medicament dispensing device 10 which is designed for emergency use, for example in the treatment of battlefield wounds. A medicament dispensing device 10 configured for manual actuation may include a plunger extension 32 which may optionally have a thumb pad 34. The plunger extension 32 can be configured to have a diameter of less than the diameter of the carpule bore 18 at the actuation end of the carpule body 12. Accordingly, the plunger extension, as is shown in FIGS. 3 and 4, can be made to interface with and transfer applied force to the plunger actuator 22. Thus, in an emergency setting the user of this embodiment of the medicament dispensing device 10 may self-dispense medicament by engaging the plunger extension 32 with the plunger actuator 22 and manually applying force on the thumb pad 34.

In embodiments of the medicament dispensing device 10 which include a plunger extension 32, the plunger extension 32 may be loosely attached to the carpule body 12 with an attachment ring 36 and connector 37. The attachment ring 36 may be slidably engaged with the outside surface of the carpule body 18 such that the plunger extension may be readily slid axially into the carpule bore 18 when the medicament dispensing device 10 is actuated. Although the attachment ring 36 and plunger extension 32 are illustrated in FIGS. 3 and 4 as a cylindrical plunger extension 32 and a ring-shaped attachment ring 36, other configurations of this apparatus are within the scope of the present disclosure. For example, the plunger extension 32 may be fabricated with a cross-sectional shape which is not cylindrical. Furthermore, any structure suitable to attach the plunger extension 32 to the carpule body 12 will be suitable for the implementation of any embodiment of the medicament dispensing device 10, which includes an optional attachment between the plunger extension and body 12.

Returning to FIG. 1, it may be noted that the medicament dispensing device 10 may include a wound depth scale 38 associated with the carpule body 12 near the dispensing end 14. The wound depth scale 38 may be a relatively simple series of bands, lines or other indicia placed around the carpule body 12. Alternatively, the wound depth scale 38 may be configured to provide more sophisticated information, and could for example include selected depth measurement information. The wound depth scale 38 may optionally be color-coded, or have other features designed to enhance the visibility and readability of the wound depth scale 38 in use.

Similarly, the medicament dispensing device 10 may include a dosage scale 40 which will typically be associated with the actuation end 16 of the carpule body 12. It is within the scope of the present disclosure, however, to have the dosage scale placed elsewhere on the carpule body 12. One example of a dosage scale which is particularly well suited for the implementation of the medicament dispensing device 10 is illustrated in FIGS. 1-4. The illustrated embodiment of a dosage scale is not intended to be limiting upon the scope of the present disclosure. The representative dosage scale 40 of FIGS. 1-4 includes selected indicia 42 associated with a notch 44. The notch 44 may be defined by suitable openings in the carpule body 12 at the actuation end 16. As is best shown on FIG. 2, in this embodiment the plunger actuator 22 may include one or more tabs 46 configured to be received in and slide within the notch 44.

One or more selected portions of the tab 46 may be used in conjunction with the indicia 42 to determine dosage. For example, as is shown in FIG. 2 the edge of the tab 46 which is toward the dispensing end 14 corresponds with the upper indicia 42, indicating that the medicament dispensing device 10 as configured in FIG. 2 has not been used to dispense medicament. As described in detail below, the process of dispensing medicament involves moving the plunger actuator 22 toward the dispensing end 14. Accordingly, as a specific amount of medicament is dispensed, the bottom edge of tab 46 will correspond with specific indicia 42. As will be readily apparent from the examination of FIG. 2, when the plunger actuator 22 is fully depressed, the bottom edge of the notch 44 will correspond with the bottom indicia 42, indicating that a full dosage of the selected medicament has been administered.

The carpule body at the bottom of the notch 44 may define a stop 48 which can engage with the tab 46 to define the full possible range 50 of plunger 20 motion. Alternatively, a separate stop structure may be used to implement this feature. It is important to note that the range 50 of plunger motion is directly related to the quantity of medicament dispensed. Accordingly, a maximum quantity of medicament to be dispensed may be selected and determined by using the stop 48 or similar structure to define a selected plunger travel range 50 which corresponds to the desired full dosage.

As is best shown on FIG. 2 the plunger tip 26 may have substantially the same diameter as the orifice 28. The complete and effective dispensing of medicament, and the avoidance of apparatus jams may be enhanced if the plunger tip 26 has a concave surface facing the orifice. A concave-shovel head at the plunger tip 26 may be provided which is advantageous for dispensing powdered medicaments. It may also be noted on FIG. 1 that the carpule body 12 at the dispensing end 14 may include a selected taper 52 which may be a rounded or flattened taper 52 selected to achieve specific therapeutic goals. In certain embodiments the dispensing end 14 may be a very rigid and non-deformable end which can facilitate insertion.

Optionally, the central axis of the carpule body 12 at the dispensing end may be angled from the central axis of the carpule body 12 at the actuation end 16. It should be noted that any angle or curvature of the body 12 is entirely optional, and may be selected to achieve specific therapeutic goals. However, it has been determined that the angle between the axis of the body at the actuation end 16 and dispensing end 14 of between 100 and 120 degrees is advantageous for certain of the treatments described below. More particularly, a body angle of 115 degrees has been determined to be advantageous. A representative angular displacement 54 along the carpule body 12 is shown in FIG. 1. As shown in FIG. 1, the angular displacement 54 may be accomplished with a curved carpule body 12, alternatively two or more linear segments along the carpule body 12 may be used to implement this feature.

Figure 5:
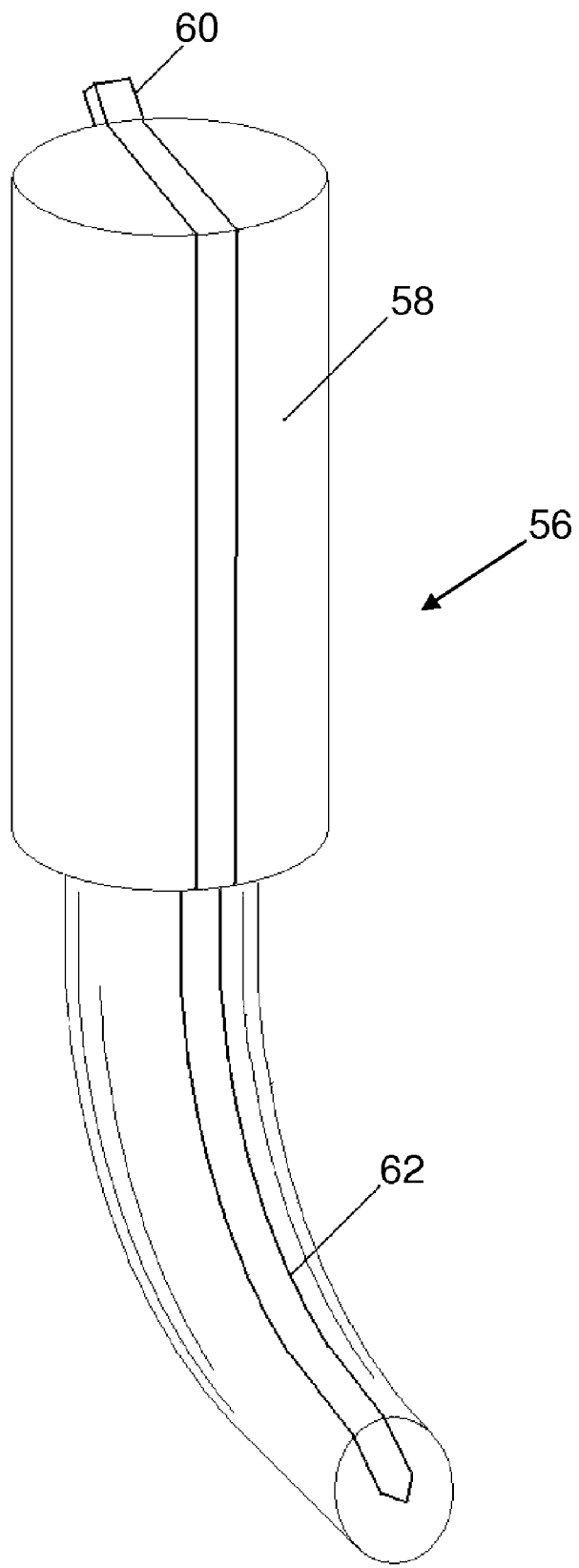
FIG. 5 is a perspective view of a protective cover configured to protect the entire medicament dispensing device of FIG. 3.

The medicament dispensing device 10 may include a protective cover 56 associated with some or all of the medicament dispensing device 10. For example, as is shown in FIG. 5 the protective cover 56 may be implemented with a sheath 58 which in use covers and seals all structures associated with any embodiment of the medicament dispensing device 10, for example, the embodiment shown in FIGS. 3 and 4. In particular, the sheath 58 may protectively cover both the carpule body 12 and the associated apparatus, any medicament contained therein, and the plunger extension 32 and associated apparatus. The sheath 58 may include apparatus or structures which facilitate the easy opening of the protective cover 56. The protective cover 56 may be implemented with any known method of sealing and protecting a medical device. For example, as is shown on FIG. 5, the sheath 58 may include a tab 60 and a scored seam 62 which facilitates the opening of the protective cover 56. In use a simple pull on the tab 60 will cause sheath 58 to separate along the scored seam 62.

Figure 6:
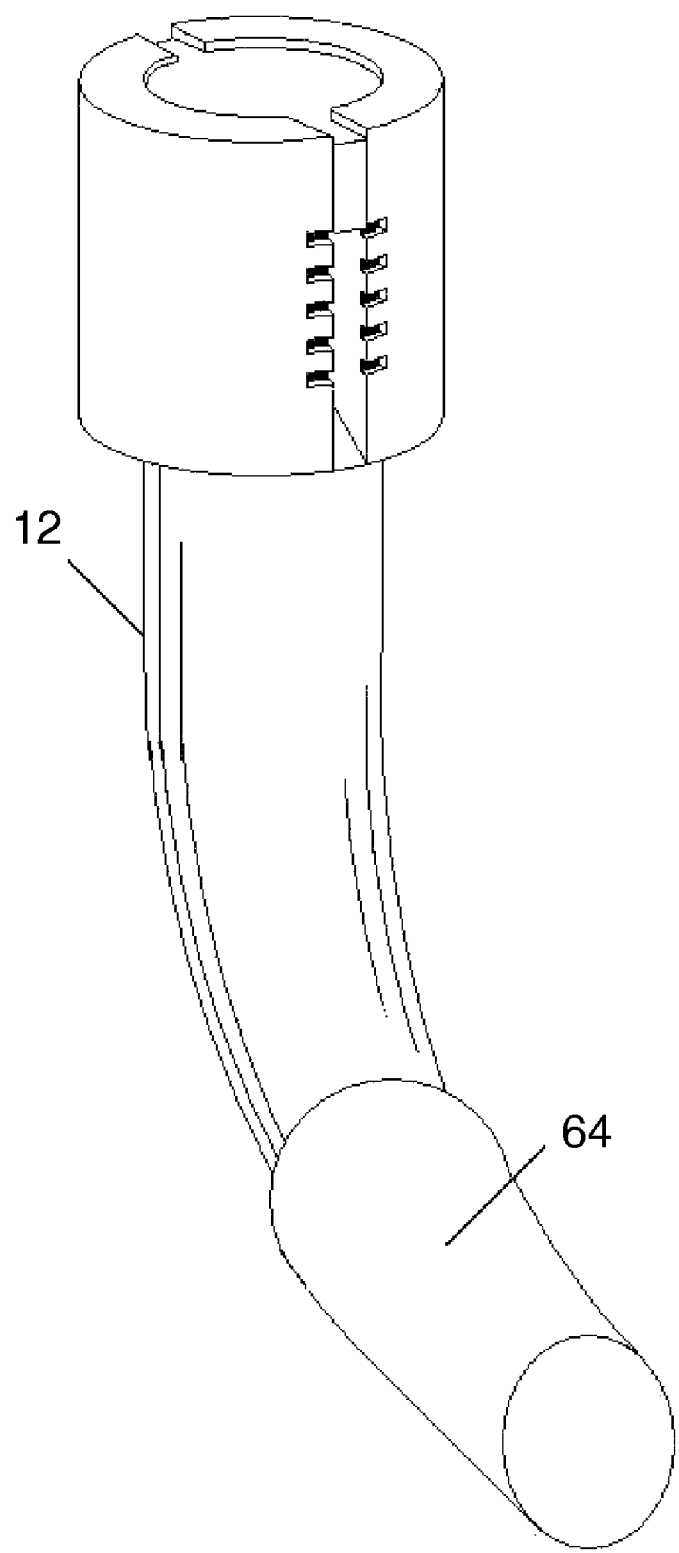
FIG. 6 is a perspective view of a protective cover configured to protect the dispensing end of the medicament dispensing device of FIG. 1.

Alternatively, the protective cover 56 may cover only a portion of the medicament dispensing device 10 and preferably, any medicament stored therein. For example as is shown on FIG. 6, the protective cover may be implemented with a partial sheath 64 associated with the dispensing end 14 of the carpule body 12.

Another embodiment disclosed herein includes a method of dispensing a medicament. In the most generalized sense the method includes providing a medicament dispensing device 10 such as is described above. A medicament dispensing device 10 includes a plunger 20 operatively associated with a carpule bore 18 such that the plunger tip 26 and an orifice 28 associated with a dispensing end 14 of the carpule bore 18 together define a medicament volume 29 at the dispensing end 14. The medicament dispensing device 10 will typically be provided pre-loaded with a select type and quantity of medicament. The medicament may be a powdered antibiotic, gel, liquid, or other substance in any dispensable form which has desired therapeutic properties.

In use the medicament dispensing device 10 may be inserted into a site to a selected depth. The depth may be verified using a wound depth scale 38 associated with the medicament dispensing device 10. When the medicament dispensing device is inserted into the site to an appropriate depth, the plunger may be depressed to dispense the medicament into the site.

As used herein, site means any location on a human or animal subject where it is desired to dispense a medicament. For example, the site may be a wound. Alternatively, the site may be a non-traumatized location on a human or animal subject, such as a periodontal pocket. Thus, the method may include the treatment of traumatic injuries such as bullet wounds or non-emergency conditions such a periodontal disease.

The size and configuration of the medicament dispensing device 10 may be adapted for specific treatment goals. For example, in one embodiment for the treatment of periodontal disease the orifice 28 is approximately 1.3 mm in diameter and the plunger travel range is set to approximately 2-10 mm. Thus, this embodiment is configured to dispense approximately 2-10 mg. of medicament at a site.

The medicament dispensing device 10 may be manufactured from any suitably rigid material, however various plastic polymers including, but not limited to, polyethylene, polypropylene, nylon or other plastics which are relatively easy and inexpensive to manufacture, and are easily sterilized. These and similar plastics are particularly well-suited for the fabrication of a medicament dispensing device 10 and associated apparatus.

As described above, the plunger 20 of the medicament dispensing device 10 may be actuated with a medicament dispensing gun, or manually. If a medicament dispensing gun is the desired means of actuation, (for example when treating a non-emergency condition such as periodontal disease) the method will include loading the medicament dispensing device 10 into a suitable medicament dispensing gun. The medicament dispensing device 10 may be engaged with a socket associated with the gun at an enlarged head 30 associated with the medicament dispensing device 10. The dispensing end 14 of the medicament dispensing device 10 may then be inserted into the site to a selected depth as observed on the wound depth scale 38. Thereupon, the plunger 20 may be actuated thus dispensing the medicament by depressing a trigger associated with the medicament dispensing gun.

Alternatively, an embodiment of the medicament dispensing device 10 configured for self treatment or use in emergency settings may be used to implement the described methods. For example, the medicament dispensing device 10 may include a plunger extension 32 as shown in FIGS. 3 and 4 plus associated apparatus which facilitate the selective actuation of the plunger with a user's thumb. This embodiment is particularly well-suited for the self treatment, or the treatment by untrained personnel of battlefield-type wounds such as are suffered by soldiers and police officers. In this embodiment, the medicament dispensing device 10 may be utilized to dispense a topical antibiotic (which may be a powdered antibiotic) into a bullet or other wound thus preventing infection, gangrene, and the potential loss of life or limb.

In an emergency situation as described above, the medicament may be dispensed by placing the medicament dispensing device 10 into a wound to a desired depth as viewed on a wound depth scale 38. The medicament may then be readily dispensed by depressing the plunger extension 32 with the user's thumb. If the medicament dispensing device 10 is equipped with a dosage scale 40 as described above a full or partial dosage of medicament may be readily administered. The dispensing of a full dosage may be facilitated by including a stop 48 in association with the actuation apparatus.

Any embodiment of the medicament dispensing device 10 may include a protective cover 56. Assuming that a protective cover 56 is provided, the method will also include removing the protective cover prior to utilizing the device. The protective cover 56 may be easily removed by pulling on a tab 60, breaking open a sheath 58 along a scored seam 62. Alternatively, other methods of opening a protective cover may be utilized to access the medicament dispensing device 10.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference. The disclosure also encompasses all possible permutations of the claim set, as if they were multiple dependent claims.

What is claimed is:

1. A medicament dispensing device comprising:
   a substantially rigid carpule body having a dispensing end and an actuation end opposite the dispensing end, the carpule body further defining a carpule bore;
   a plunger operatively disposed within the carpule bore having a plunger actuator near the actuation end;
   a plunger tip opposite the plunger actuator;
   a medicament volume defined by the carpule bore between the plunger tip and an orifice at the dispensing end;
   a wound depth scale operatively associated with the dispensing end of the carpule body, the wound depth scale comprising indicia placed upon an outer surface of the carpule body; and
   a dosage scale operatively associated with the actuation end of the carpule body, wherein the wound depth scale and the dosage scale are separate from each other.

2. The medicament dispensing device of claim 1 wherein the actuation end further comprises an enlarged head adapted to be received in a medicament dispensing gun.

3. The medicament dispensing device of claim 1 further comprising a plunger extension engageable with the plunger actuator to provide for manual actuation of the plunger actuator.

4. The medicament dispensing device of claim 3 further comprising an attachment ring connecting the plunger extension in sliding engagement with the carpule body.

5. The medicament dispensing device of claim 1 wherein the dosage scale comprises indicia associated with a notch, the notch further being operatively associated with the plunger actuator, which indicia indicate selected delivery of a partial dosage of a medicament.

6. The medicament dispensing device of claim 5 further comprising a stop associated with the notch defining a limit to the travel of the plunger actuator which is associated with the delivery of a full dosage of the medicament.

7. The medicament dispensing device of claim 1 wherein the plunger tip has substantially the same diameter as the orifice.

8. The medicament dispensing device of claim 1 wherein the plunger tip defines a concave surface facing the orifice.

9. The medicament dispensing device of claim 1 wherein the carpule body proximate the dispensing end is tapered.

10. The medicament dispensing device of claim 1 wherein the axis of the carpule body at the dispensing end is angled from the axis of the carpule body at the actuation end.

11. The medicament dispensing device of claim 1 wherein the axis of the carpule body at the dispensing end is angled from the axis of the carpule body at the actuation end at an angle of between 100 and 120 degrees.

12. The medicament dispensing device of claim 1 further comprising a protective cover associated with the carpule body.

13. The medicament dispensing device of claim 12 wherein the protective cover covers the entire carpule body.

14. The medicament dispensing device of claim 13 wherein the protective cover comprises:
    a tab, and
    a scored seam facilitating the opening of the protective cover.

15. The medicament dispensing device of claim 12 wherein the protective cover covers the dispensing end of the carpule body.

16. A method of dispensing a medicament comprising:
    providing a medicament dispensing device comprising a substantially rigid carpule body having a dispensing end and an actuation end opposite the dispensing end, the carpule body further defining a carpule bore, a plunger operatively associated with a measured quantity of a medicament being disposed within the carpule bore and having a plunger actuator near the actuation end and a plunger tip opposite the plunger actuator, a wound depth scale comprising indicia placed upon an outer surface of the carpule body associated with the dispensing end of the carpule body; and a dosage scale operatively associated with the actuation end of the carpule body, wherein the wound depth scale and the dosage scale are separate from each other;
    inserting the dispensing end of the carpule body into a site to a selected depth
    verifying the depth of insertion with the depth scale;
    depressing the plunger to dispense the medicament into the site; and
    verifying the dosage of the dispensed medicament with the dosage scale.

17. The method of dispensing a medicament of claim 16 wherein the plunger is depressed by the actuation of a medicament dispensing gun.

18. The method of dispensing a medicament of claim 16 wherein the plunger is depressed by the manual actuation of a plunger extension.

19. The method of dispensing a medicament of claim 18 wherein the plunger extension is attached to the medicament dispensing device with a sliding attachment ring.

20. The method of dispensing a medicament of claim 16 further comprising:
   dispensing a partial dose of the medicament; and
   verifying the partial dosage with the dosage scale.

21. The method of dispensing a medicament of claim 16 further comprising dispensing a full dosage of the medicament by depressing the plunger to engagement with a plunger stop.

22. The method of dispensing a medicament of claim 16 further comprising removing a protective cover from the medicament dispensing device.

23. The medicament dispensing device of claim 1 further comprising the wound depth scale comprising indicia placed around the carpule body.

24. The medicament dispensing device of claim 2 wherein the enlarged head is substantially cylindrical.

25. The medicament dispensing device of claim 2 wherein the dosage scale is disposed upon the enlarged head.

26. The medicament dispensing device of claim 25 wherein the dosage scale comprises indicia associated with a notch, the notch further being operatively associated with the plunger actuator, which indicia indicate selected delivery of a partial dosage of a medicament.

27. The medicament dispensing device of claim 26 wherein the carpule bore extends through the enlarged head.

28. The medicament dispensing device of claim 27 wherein the notch defines a lengthwise opening in the enlarged head which is substantially aligned with a longitudinal axis of the carpule bore.

29. The medicament dispensing device of claim 1 wherein the carpule body further comprises a carpule body curvature associated with an angular displacement of the carpule body and wherein the plunger tip is extendible into the carpule body curvature.

30. The medicament dispensing device of claim 29 wherein the plunger includes a plunger curvature that corresponds to the carpule body curvature when the plunger is received within the carpule body.

* * * * *